United States Patent [19]

Confer

[11] Patent Number: 4,745,930

[45] Date of Patent: May 24, 1988

[54] FORCE SENSING INSOLE FOR ELECTRO-GONIOMETER

[75] Inventor: Richard G. Confer, Chattanooga, Tenn.

[73] Assignee: Chattanooga Corporation, Chattanooga, Tenn.

[21] Appl. No.: 919,880

[22] Filed: Oct. 16, 1986

[51] Int. Cl.⁴ ............................................. A61B 5/10
[52] U.S. Cl. .................................... 128/779; 128/782
[58] Field of Search ..................... 128/774, 749, 782; 340/573

[56] References Cited

U.S. PATENT DOCUMENTS

| | | | |
|---|---|---|---|
| 1,771,258 | 7/1930 | Kalikow et al. | 439/37 |
| 3,702,999 | 11/1972 | Gradisar | 36/139 |
| 3,791,375 | 2/1974 | Pfeiffer | 128/779 |
| 3,974,491 | 8/1976 | Sipe | 73/172 |
| 4,426,884 | 1/1984 | Polchaninoff | 128/779 |
| 4,503,705 | 3/1985 | Polchaninoff | 73/172 |
| 4,647,918 | 3/1987 | Goforth | 128/779 |

OTHER PUBLICATIONS

Brochure entitled "Membrane Switches", published by GM Nameplate, Inc., Sep. 1982, 4 pages.

Primary Examiner—Kyle L. Howell
Assistant Examiner—Randy Citrin
Attorney, Agent, or Firm—Bell, Seltzer, Park & Gibson

[57] ABSTRACT

A force sensing insole is disclosed which is adapted to be used in association with an electro-goniometer for analyzing the gait of a patient. The insole includes a body member composed of three overlying sheets of thin plastic material which are bonded together, with the intermediate sheet having cut-outs in each of the heel, ball and toe portions so as to define three separate internal chambers. A contact switch is positioned in each of the open chambers, and which comprises a plurality of parallel fingers formed of conductive ink on the inwardly facing surface of one of the outer sheets, and an area of conductive material on the inwardly facing surface of the outer sheet. The body member includes a laterally extending flexible strip, and which is adapted to flex and extend outwardly from the wearer's shoe. Also, lines of conductive ink are provided in the body member which extend from each of the contact switches to a terminal positioned at the end of the strip.

18 Claims, 2 Drawing Sheets

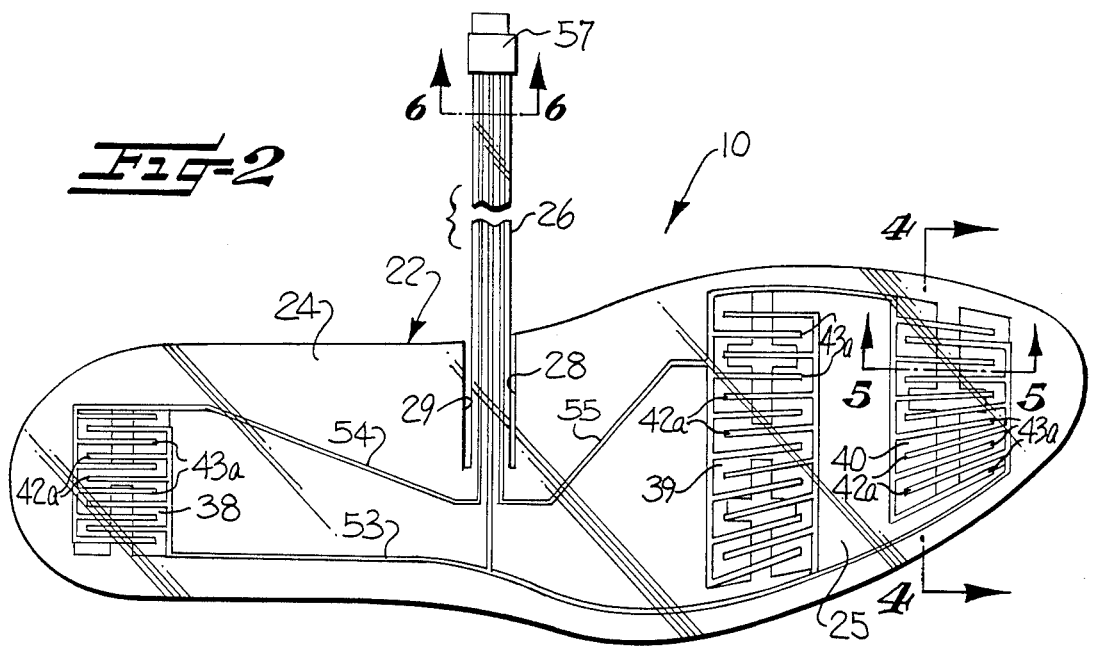
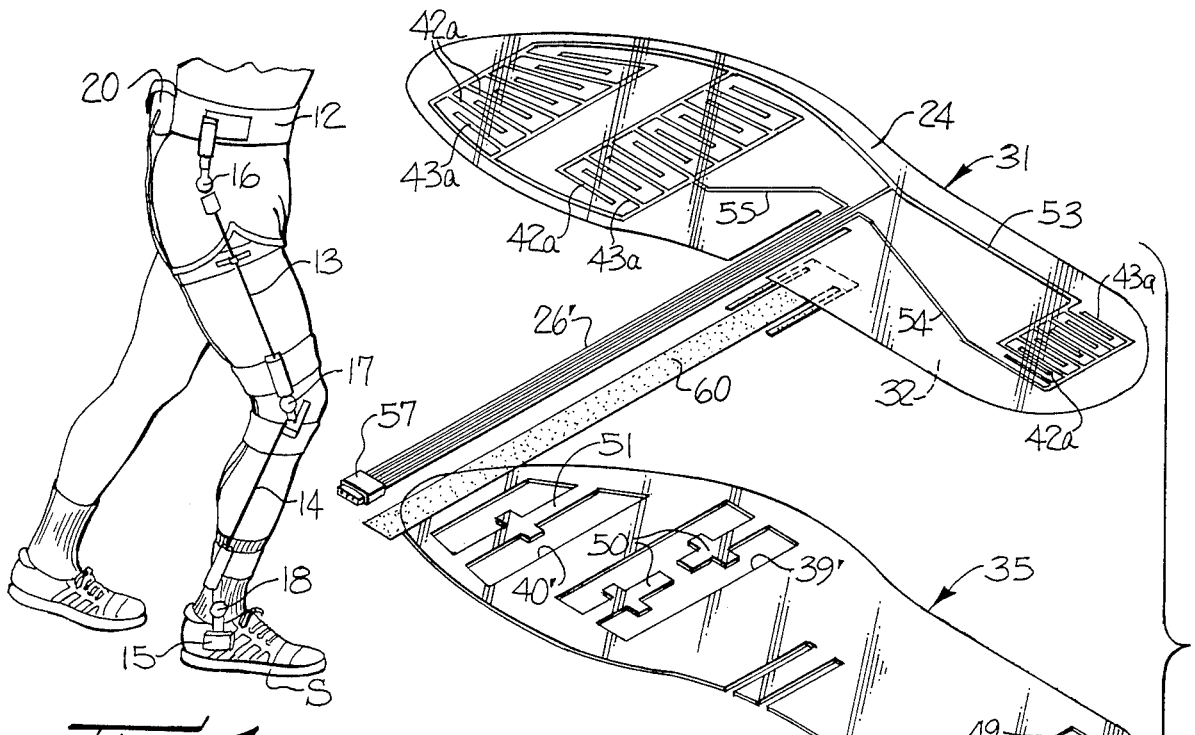
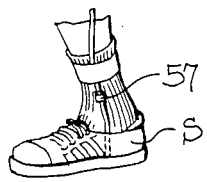
Fig-1
Fig-1A
Fig-2
Fig-3

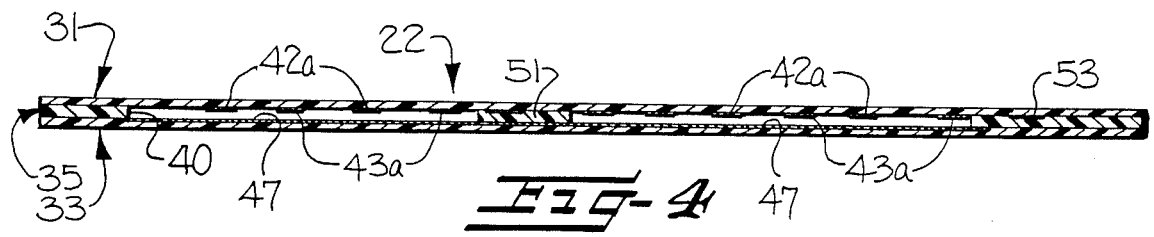
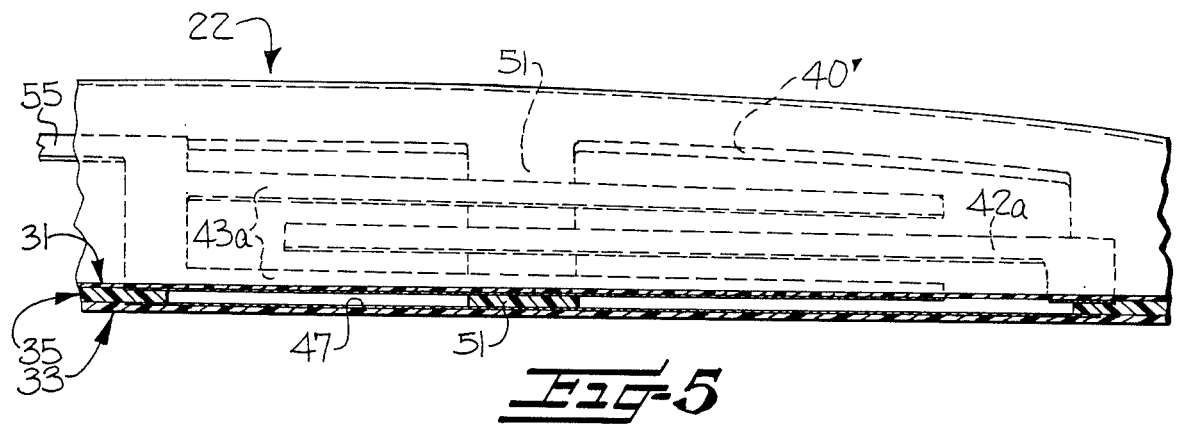
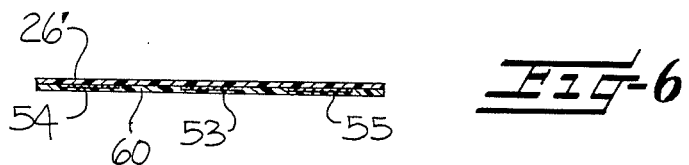
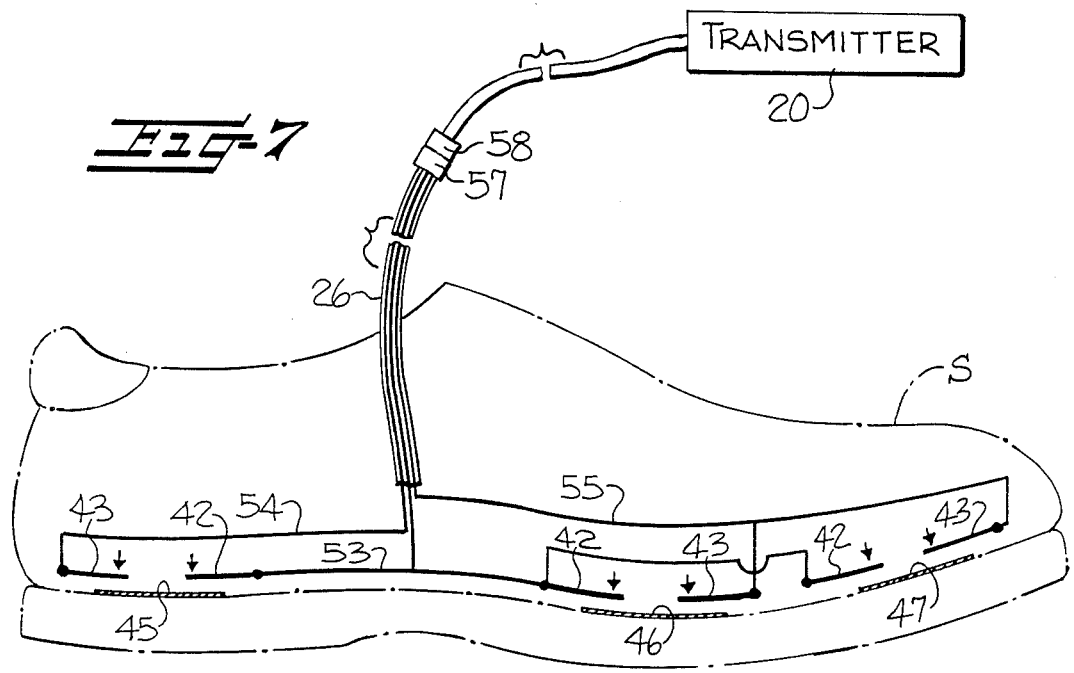

FORCE SENSING INSOLE FOR ELECTRO-GONIOMETER

BACKGROUND OF THE INVENTION

The present invention relates to a force sensing insole which is adapted to be placed inside a shoe so as to provide electrical signals which are useful in the analysis of the walking or running gait of the wearer.

In recent years, devices for the electronic recording of human joint motions have been developed and which are useful in determining the functional level of a patient. One such present device, commonly referred to as an electro-goniometer, permits three mutually orthogonal rotations to be recorded, namely at the hip, knee, and ankle of a patient. These measurements are achieved by the use of precision potentiometers which serve as motion transducers, and the outputs of the potentiometers are transmitted to a recording device which records the signals on a strip chart. A device of this general type is currently marketed by Chattex Corporation of Chattanooga, Tenn., under the trademark "TRIAX". The "TRIAX" electro-goniometer also includes a foot switch which is attached to the bottom of a standard tennis shoe, and which is worn by the patient during testing. The foot switch generates signals which are representative of the timing of the heel strike, heel lift off, ball strike, and ball lift off, which are also useful in the gait analysis.

While the present "TRIAX" electro-goniometer has proven to be useful in many applications, the design of the foot switch has been a source of difficulty, since the position of the switch on the bottom of the standard tennis shoe often changes the relative elevation between the two shoes of the wearer, which in turn may alter the gait of the wearer.

It is accordingly an object of the present invention to provide a foot switch for an electro-goniometer which avoids the above noted disadvantage of the present design.

It is a more particular object of the present invention to provide a force sensing insole which is adapted for use as a foot switch with an electro-goniometer, which is of simple and inexpensive construction, and which is adapted for use inside the patient's own footwear so as to eliminate any height differential between the wearer's shoes, and so as to also eliminate any alteration of the natural gait of the wearer.

SUMMARY OF THE INVENTION

These and other objects and advantages of the present invention are achieved in the embodiment illustrated herein by the provision of a flexible force sensing insole, which is adapted to be placed inside a shoe, and which comprises a relatively thin, flexible planar body member which is shaped to generally conform to the outline of a wearer's foot and so as to define a heel portion adapted to underlie the heel of the wearer and a forward portion adapted to underlie the ball and toe portions of the wearer's foot. The body member includes an open internal heel chamber in the heel portion and an open internal forward chamber in the forward portion of the body member.

A pair of electrical contacts is disposed in each of the internal chambers and such that the contacts of each chamber are normally separated, but may be brought into electrical contact with each other upon a compressive force being applied to the insole in alignment with the associated chamber. A plurality of electrically conductive lines are positioned in the interior of the body member, and the lines are connected to respective ones of each of the contacts. Also, an electrical terminal is mounted on the body member in electrical contact with each of the conductive lines for permitting attachment of the conductive lines to an external electrical coupler or the like.

In the preferred embodiment, the body member comprises a plurality of overlying contiguous thin sheets of dielectric material which are adhered together, and the body member also includes a laterally extending integral strip having a remote free end, and which is adapted to flex and extend outwardly from the wearer's shoe. Also, the conductive lines have portions thereof extending along the length of the strip to the electrical terminal, which is mounted at the free end of the strip. The body member is preferably composed of at least three thin solid plastic sheets, with an intermediate sheet having cut-out sections defining the open chambers. Further, in the preferred embodiment, the forward portion of the body member includes two separate internal chambers, with a pair of electrical contacts in each chamber, and with one of these two chambers being located to underlie the ball of the foot of the wearer, and the other chamber being located to underlie the toe portion of the wearer's foot.

In use, the insole is placed in the shoe of the wearer, with the strip extending upwardly from the shoe along the instep of the wearer, and so that the electrical terminal may be readily attached to an external electrical coupler or the like which is part of the electro-goniometer control system. In this regard, the plastic nature of the body member permits the periphery thereof to be trimmed by scissors, so that the insole may readily configured to closely fit in shoes of various size. Further, it will be apparent that the thin construction of the insole will change the elevation of the wearer's foot only by an imperceptible amount, and thus there is no alteration of the natural gait of the wearer.

BRIEF DESCRIPTION OF THE DRAWINGS

Some of the objects and advantages of the present invention having been stated, others will appear as the description proceeds, when taken in conjunction with the accompanying drawings, in which FIG. 1 is an environmental view illustrating an electro-goniometer positioned on a patient and which includes the force sensing insole of the present invention;

FIG. 1A is a view showing the opposite side of the front foot and shoe shown in FIG. 1;

FIG. 2 is a plan view of the force sensing insole of the present invention;

FIG. 3 is an exploded perspective view of the force sensing insole illustrated in FIG. 2;

FIGS. 4 and 6 are enlarged sectional views taken substantially along the lines 4—4, and 6—6 of FIG. 2 respectively;

FIG. 5 is a sectional perspective view taken substantially along the line 5—5 of FIG. 2; and FIG. 7 is a diagrammatic view of the insole of the present invention positioned inside the wearer's shoe.

DEATILED DESCRIPTION OF A PREFERRED EMBODIMENT

Referring more particularly to the drawings, FIG. 1 illustrates a three dimensional electro-goniometer positioned on a patient, and which includes the force sensing insole 10 of the present invention positioned in the shoe S of the patient. The electro-goniometer includes an angle measuring framework which includes a waistband 12, a thigh frame 13 attached to the leg by the thigh bands, a lower leg frame 14 attached by the lower leg bands, and a shoe attachment member 15. Three potentiometers 16, 17, 18 are positioned at the junctions of the frame members for indicating the rotational position of the hip, knee and ankle, respectively. The signals from the three potentiometers are fed through wires to a transmitter 20 which is attached to the waistband 12, and the signals are transmitted by telemetry to a central computer (not shown), which collects and analyzes the data and prints a report on a strip sheet. This portion of the electro-goniometer is conventional, and thus will not be further described.

The insole 10 of the present invention is illustrated in FIGS. 2-7, and comprises a relatively thin, flexible planar body member 22 which is shaped to generally conform to the outline of the wearer's foot. More particularly, the body member includes a rear or heel portion 24 adapted to underlie the heel of the wearer's foot, and a forward portion 25 adapted to underlie the ball and toe portions of the wearer's foot. Further, the body member includes a laterally extending integral strip 26 joined adjacent the juncture of the heel portion and forward portion, i.e., adjacent the instep portion of the insole. The strip 26 has a remote free end, and it is adapted to flex and extend outwardly from the wearer's shoe S. As best seen in FIG. 2, the strip 26 is also partly defined by a pair of parallel, laterally directed slots 28, 29 in the instep portion of the insole, which serve to increase the flexibility of the strip so that it can easily bend without creasing and extend upwardly from the shoe, note FIG. 1A.

In the illustrated embodiment, the body member 22 comprises three overlying contiguous thin sheets of solid plastic dielectric material, such as Mylar, Lexan or similar plastic, and which are adhered together. More particularly, the body member preferably has a thickness not greater than about 0.025 inches, and it is composed of an upper plastic sheet 31 having an inwardly facing surface 32, a lower plastic sheet 33 having an inwardly facing surface 34, and an intermediate plastic sheet 35. The three sheets are preferably bonded together by a suitable adhesive. In one suitable specific example, the upper and lower sheets are formed of clear Lexan plastic of 0.005 inch thickness, and the intermediate sheet is formed of clear Mylar plastic which is 0.011 inch in thickness. Thus the total thickness of the insole is about 0.021 inch. Also, the upper sheet 31 includes an integral laterally directed segment 26' which forms a portion of the strip 26.

The body member 22 also includes an open internal first or heel chamber 38 which is positioned to underlie the heel of the wearer's foot, an open internal second chamber 39 which is positioned to underlie the ball of the wearer's foot, and an open internal third chamber 40 which is adapted to underlie the toe portion of the wearer's foot. Each of the chambers 38, 39, 40 is of generally rectangular outline, and each is sized so as to extend laterally across substantially the entire lateral width of the body member. In addition, the chambers are defined by cut-out sections 38', 39', 40' formed in the intermediate sheet 35, as best seen in FIG. 3. By this arrangement, it will be seen that each of the open chambers includes opposing, normally spaced apart inner surfaces defined by portions of the inwardly facing surfaces 32, 34 of the two outer sheets, and these opposing inner surfaces are spaced apart a distance which conforms to the thickness of the intermediate sheet.

A contact switch which is composed of a pair of electrical contacts 42, 43 is disposed in each internal chamber of the body member, and such that the contacts of each pair are normally electrically separated but may be brought into electrical contact with each other upon a compressive force being applied to the insole in alignment with the associated chamber. The pair of contacts in each chamber comprises a plurality of laterally spaced apart fingers extending in a lateral row across the chamber, with alternate fingers 42a being part of the contact 42, and the intervening fingers 43a being part of the other contact 43. Also, the fingers take the form of a printed conductive ink which is adhered to the inwardly facing surface 32 of the upper sheet 31. The inwardly facing surface 34 of the sheet 33 has areas 45, 46, 47 of electrically conductive material printed thereon which are aligned with each of the three chambers 38, 39, 40, and so that the fingers are adapted to be moved into contact with the conductive material upon a compressive force being applied to the associated chamber, and such that the fingers of the two contacts 42, 43 will be in electrical communication across the conductive material.

In the preferred embodiment, each of the chambers 38, 39, 40 also includes a dielectric separator pad 49, 50, 51 disposed between a portion of each of the fingers and the conductive material, and so as to normally maintain the row of fingers separated from the conductive material. As illustrated, this separator pad comprises an integral portion of the intermediate sheet which extends laterally across a major portion of the associated chamber, note FIG. 3.

The insole 10 further includes a total of three electrically conductive lines 53, 54, 55 positioned in the interior of the body member and which are connected to respective ones of each of the contacts of each of the open chambers. The line 53 is connected to the contact 42 of each of the pair of contacts, and the second line 54 is connected to the other contact 43 in the heel chamber 38. Finally, the third line 55 is connected to the other contact 43 in both of the second and third chambers 39, 40. Further, portions of the three lines extend along the length of the strip 26 to the free end thereof, and an electrical terminal 57 is mounted at the free end which is in electrical contact with each of the conductive lines for permitting attachment of the conductive lines to an external electrical coupler 58 or the like, note FIGS. 1A and 7. The conductive lines are preferably composed of a conductive ink which has been printed on the inwardly facing surface 32 of the upper sheet 31 prior to the lamination of the three sheets.

The method of fabricating the insole 10 of the present invention is best described with reference to FIG. 3. In particular, the three sheets 31, 33, 35 are initially prepared, with the inwardly facing surface 32 of the upper sheet 31 having the rows of fingers 42a, 43a and conductive lines 53, 54, 55 printed thereon. A separate narrow plastic piece 60 may then be adhesively applied to the underside of the strip, so as to cover and protect the conductive lines thereon. Also, the areas of conductive material 45, 46, 47 are applied to the inwardly facing surface 34 of the lower sheet 33, and the cut-outs 38', 39', 40' are formed in the intermediate sheet 35 and which define the three internal chambers. The three sheets are then brought together and secured by means of a suitable adhesive or heat sealing. The final outline may then be cut, together with the two laterally extending slots 28, 29. Finally, the terminal 57 is attached to the free end of the strip 26 in a conventional manner, and so that the terminal is in electrical contact with each of the conductive lines 53, 54, 55.

As will be apparent from FIG. 2, all of the open chambers 38, 39, 40 are spaced from the periphery of the body member, and thus the periphery of the body member is adapted to be trimmed by scissors to permit the insole to fit varying shoe sizes. This renders the insole easy to install and very adaptable from shoe size to shoe size. The operation of each of the contact switches of the insole is similar to that of a touch switch, wherein pressure applied by the ball or heel of the foot causes the fingers of the contacts to engage the area of conductive material and thus close. Also, the relatively large size of each of the switches permits a significant amount of misalignment of the ball and heel of the foot with respect to the switches, yet assuring that the switch will activate. The presence of the third internal chamber 40 below the toe portion of the wearer's foot assures that when pressure is relieved from the ball of the foot and moves forwardly toward the front of the foot, the switch in the third chamber will be closed to provide an indication of this continued forward movement. It will also be apparent that the insole 10 is equally useful in the other shoe of the patient, by simply turning it over so that the sheet 31 engages the bottom of the shoe.

In the drawings and specification, there has been set forth a preferred embodiment of the invention, and although specific terms are employed, they are used in a generic and descriptive sense only and not for purposes of limitation.

That which I claim is:

1. A flexible force sensing insole adapted to be placed inside a shoe to permit an analysis of the walking or running gait of the wearer, comprising a relatively thin, flexible planar body member shaped to generally conform to the outline of a wearer's foot and so as to define a heel portion adapted to underlie the heel of the wearer's foot, a forward portion adapted to underlie the ball and toe portions of the wearer's foot, and a laterally extending integral strip having a remote free end and which is adapted to flex and extend outwardly from the wearer's shoe, said body member including an open internal heel chamber in said heel portion and an open internal forward chamber in said forward portion, with each of said chambers including opposing, normally spaced apart inner surfaces, contact switch means including a pair of electrical contacts disposed in each of said chambers of said body member such that said contacts of each pair are actuated upon a compressive force being applied to said insole in alignment with the associated chamber, with each of said pair of electrical contacts comprising a plurality of parallel, laterally spaced apart fingers extending in a row across the associated chamber, with alternate fingers being part of one of the electrical contacts and intervening fingers being part of the other electrical contact, and with the row of fingers being adhered to one of said opposing inner surfaces of the associated chamber, and an area of electrically conductive material on the opposing inner surface of each chamber, so that the fingers are adapted to be moved into contact with said conductive material upon a compressive force being applied to the insole in alignment with the associated chamber to establish electrical contact between adjacent fingers, a plurality of electrically conductive lines positioned in said body member and connected to respective ones of each of said contacts, with said lines having portions thereof extending along the length of said strip to said free end thereof, and electrical terminal means mounted on the free end of said strip and in electrical contact with each of said conductive lines for permitting attachment of said conductive lines to an external electrical coupler.

2. The flexible force sensing insole as defined in claim 1 wherein said fingers of said contact switch means comprise a conductive ink which has been printed on said one inner surface.

3. The flexible force sensing insole as defined in claim 2 wherein each of said chambers includes a dielectric separator pad disposed between a portion of each of said fingers and said conductive material, so as to assist in maintaining the row of fingers separated from said conductive material in the absence of a compressive force.

4. The flexible force sensing insole as defined in claim 1 wherein each of said chambers, and each of said rows of fingers extend laterally across at least the major portion of the width of said body member.

5. The flexible force sensing insole as defined in claim 4 wherein each of said open chambers is spaced from the periphery of said body member, such that the periphery of said body member is adapted to be trimmed to permit the insole to fit varying shoe sizes.

6. The flexible force sensing insole as defined in claim 1 wherein said body member comprises a plurality of overlying contiguous thin sheets of dielectric material which are adhered together, and said sheets of said insole are each composed of a solid plastic material.

7. The force sensing insole as defined in claim 1 wherein said strip is defined in part by a pair of parallel, laterally directed slots which extend into said body member adjacent the juncture of said heel portion and said forward portion.

8. A flexible force sensing insole adapted to be placed inside a shoe to permit an analysis of the walking or running gait of the wearer, comprising a relatively thin, flexible planar body member shaped to generally conform to the outline of a wearer's foot, said body member comprising at least three overlying contiguous sheets of dielectric thin plastic material which are adhered together, with an intermediate one of said sheets having cut-out sections which define an open first chamber which is positioned to underlie the heel of the wearer's foot, an open second chamber which is positioned to underlie the ball of the wearer's foot, and an open third chamber which is adapted to underlie the toe portion of the wearer's foot, contact switch means including a pair of electrical contacts disposed in each of said chambers of said body member such that the pair of contacts of each chamber are normally electrically separated but may be brought into electrical contact upon a compressive force being applied to said insole in alignment with the associated chamber, and means including a plurality of electrically conductive lines positioned in the interior of said body member and connected to respective ones of each of said electrical contacts for electrically connecting the same to a signal processor.

9. The flexible force sensing insole as defined in claim 8 wherein said insole has a total thickness not greater than about 0.025 inches.

10. The flexible force sensing insole as defined in claim 8 wherein each of said open chambers is defined by opposing, normally spaced apart inner surfaces, and each of said pair of contacts comprises a conductive ink which has been printed on one of said opposing inner surfaces, and each of said contact switch means further comprises an area of electrically conductive material positioned on the opposing inner surface of each chamber.

11. The flexible force sensing insole as defined in claim 10 wherein each of said conductive lines comprises a conductive ink which has been printed on an interior surface of one of said sheets.

12. The flexible force sensing insole as defined in claim 8 wherein there are three of said conductive lines, with one of said lines being connected to one of said contacts of each pair of contacts, with a second of said lines being connected to the other contact in said first chamber, and with the third of said lines being connected to the other contact in both said second and third chambers.

13. The flexible force sensing insole as defined in claim 8 wherein said body member further includes a laterally extending integral strip having a remote free end which is adapted to flex and extend outwardly from the wearer's shoe, and wherein said conductive lines have portions thereof which extend along said strip, and further comprising electrical terminal means mounted at said free end of said strip and being in electrical contact with each of said conductive lines.

14. The flexible force sensing insole as defined in claim 8 wherein each of said first, second, and third chambers extends laterally across said body member for a substantial portion of its width and is defined by opposing, normally spaced apart inner surfaces, and wherein said pair of contacts in each chamber comprises a plurality of parallel, laterally spaced apart fingers extending in a laterally directed row across said chamber, with alternate fingers being part of one of the contacts and intervening fingers being part of the other contact, and with the row of fingers being adhered to one of said opposing inner surfaces, and with the other opposing inner surface of each chamber having an area of electrically conductive material thereon, so that the fingers are adapted to be moved into contact with said conductive material upon a compressive force being applied to said insole in alignment with the associated chamber to establish electrical contact between adjacent fingers.

15. A flexible force sensing insole adapted to be placed inside a shoe to permit an analysis of the walking or running gait of the wearer, comprising a relatively thin, flexible planar body member shaped to generally conform to the outline of a wearer's foot and so as to define a heel portion adapted to underlie the heel of the wearer's foot, a forward portion adapted to underlie the ball and toe portions of the wearer's foot, and a laterally extending integral strip having a remote free end which is adapted to flex and extend outwardly from the wearer's shoe, said body member including an open internal heel chamber in said heel portion and an open internal forward chamber in said forward portion, and said body member comprising a plurality of overlying contiguous thin sheets of dielectric material which are adhered together, and with said sheets being each composed of a solid plastic material, contact switch means including a pair of electrical contacts disposed in each of said chambers of said body member such that said contacts of each pair are actuated upon a compressive force being applied to said insole in alignment with the associated chamber, a plurality of electrically conductive lines positioned in said body member and connected to respective ones of each of said contacts, with said lines having portions thereof extending along the length of said strip to said free end thereof, and electrical terminal means mounted on the free end of said strip and in electrical contact with each of said conductive lines for permitting attachment of said conductive lines to an external electrical coupler.

16. A flexible force sensing insole adapted to be placed inside a shoe to permit an analysis of the walking or running gait of the wearer, comprising a relatively thin, flexible palanar body member shaped to generally conform to the outline of a wearer's foot and so as to define a heel portion adapted to underlie the heel of the wearer's foot, a forward portion adapted to underlie the ball and toe portions of the wearer's foot, and a laterally extending integral strip having a remote free end and which is adapted to flex and extend outwardly from the wearer's shoe, with said strip being defined in part by a pair of parallel, laterally directed slots which extend into said body member adjacent the juncture of said heel portion and said forward portion, said body member including an open internal heel chamber in said heel portion and an open internal forward chamber in said forward portion, contact switch means including a pair of electrical contacts disposed in each of said chambers of said body member and such that said contacts of each pair are actuated upon a compressive force being applied to said insole in alignment with the associated chamber, a plurality of electrically conductive lines positioned in the interior of said body member and connected to respective ones of each of said contacts, with said lines having portions thereof extending along the length of said strip to said free end thereof, and electrical terminal means mounted on the free end of said strip and in electrical contact with each of said conductive lines for permitting attachment of said conductive lines to an external electrical coupler.

17. A flexible force sensing insole adapted to be placed inside a shoe to permit an analysis of the walking or running gait of the wearer, comprising a relatively thin, flexible planar body member shaped to generally conform to the outline of a wearer's foot, said body member comprising a plurality of overlying contiguous sheets of dielectric material which are adhered together, said body member including an open first chamber which is positoned to underlie the heel of the wearer's foot, an open second chamber which is positioned to underlie the ball of the wearer's foot, and an open third chamber which is adapted to underlie the toe portion of the wearer's foot, contact switch means including a pair of electrical contacts disposed in each of said chambers of said body member such that the pair of contacts of each chamber are normally electrically separated but may be brought into electrical contact upon a compressive force being applied to said insole in alignment with the associated chamber, and means including three electrically conductive lines positioned in said body member and connected to respective ones of each of said electrical contacts for electrically connecting the same to a signal processor, with one of said lines being connected to one of said contacts of each pair of contacts, with a second of said lines being connected to the other contact in said first chamber, and with the third of said lines being connected to the other contact in both said second and third chambers.

18. A flexible force sensing insole adapted to be placed inside a shoe to permit an analysis of the walking or running gait of the wearer, comprising a relatively thin, flexible planar body member shaped to generally conform to the outline of a wearer's foot, said body member comprising a plurality of overlying contiguous sheets of dielectric material which are adhered together, said body member including an open first chamber which is positioned to underlie the heel of the wearer's foot, an open second chamber which is positioned to underlie the ball of the wearer's foot, and an open third chamber which is adapted to underlie the toe portion of the wearer's foot, with each of said first, second, and third chambers extending laterally across said body member for a substantial portion of its width and being defined by opposing, normally spaced apart inner surfaces, contact switch means including a pair of electrical contacts disposed in each of said chambers of said body member such that the pair of contacts of each chamber are normally electrically separated but may be brought into electrical contact upon a compressive force being applied to said insole in alignment with the associated chamber, with each of said pair of contacts in each chamber comprising a plurality of parallel, laterally spaced apart fingers extending in a laterally directed row across said chamber, with alternate fingers being part of one of the contacts and intervening fingers being part of the other contact, and with the row of fingers being adhered to one of said opposing inner surfaces, and with the other opposing inner surface of each chamber having an area of electrically conductive material thereon, so that the fingers are adapted to be moved into contact with said conductive material upon a compressive force being applied to said insole in alignment with the associated chamber to establish electrical contact between adjacent fingers, and means including a plurality of electrically conductive lines positioned in said body member and connected to respective ones of each of said electrical contacts for electrically connecting the same to a signal processor.

* * * * *